United States Patent [19]

Ackermann et al.

[11] 4,309,555

[45] Jan. 5, 1982

[54] NOVEL CYCLOPROPANE DERIVATIVES

[75] Inventors: Peter Ackermann, Reinach; Jozef Drabek, Oberwil; Saleem Farooq, Ettingen; Laurenz Gsell, Basel; Rudolf Wehrli, Kheinfelden, all of Switzerland

[73] Assignee: Ciba-Geigy Corporation, Ardsley, N.Y.

[21] Appl. No.: 214,814

[22] Filed: Dec. 9, 1980

[30] Foreign Application Priority Data

| | | | |
|---|---|---|---|
| Dec. 21, 1979 | [CH] | Switzerland | 11407/79 |
| Jun. 20, 1980 | [CH] | Switzerland | 4751/80 |
| Oct. 27, 1980 | [CH] | Switzerland | 7995/80 |

[51] Int. Cl.$^3$ ............................ C07F 7/10; C07F 7/18

[52] U.S. Cl. .................................... 556/417; 560/124; 424/184

[58] Field of Search ......................................... 556/417

[56] References Cited

U.S. PATENT DOCUMENTS

| | | | |
|---|---|---|---|
| 2,657,226 | 10/1953 | Frisch et al. | 556/417 |
| 2,776,306 | 1/1957 | Cole | 556/417 X |
| 2,985,679 | 5/1961 | Pepe | 556/417 X |
| 3,274,155 | 9/1966 | Saunders et al. | 556/417 X |

FOREIGN PATENT DOCUMENTS

| | | | |
|---|---|---|---|
| 2506798 | 8/1976 | German Democratic Rep. | 556/417 |
| 2506805 | 8/1976 | German Democratic Rep. | 556/417 |
| 1227428 | 4/1971 | United Kingdom | 556/417 |

*Primary Examiner*—Paul F. Shaver
*Attorney, Agent, or Firm*—Frederick H. Rabin

[57] ABSTRACT

1-(Dicyano-trimethylsiloxy)methyl-2,2-dimethylcyclopropane derivatives of the formula

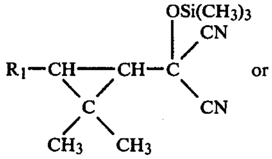

or

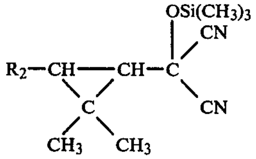

wherein $R_1$ is

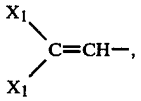

$R_2$ is

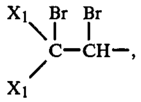

and $X_1$ is halogen.

A process for the production of these compounds and their use as intermediates for obtaining biocidal compounds is described.

6 Claims, No Drawings

NOVEL CYCLOPROPANE DERIVATIVES

The present invention relates to 1-(dicyano-trimethylsiloxy)methyl-2,2-dimethylcyclopropane derivatives, to the production thereof, and to the use thereof as intermediates for obtaining biocidal compounds.

The 1-(dicyano-trimethylsiloxy)methyl-2,2-dimethylcyclopropane derivatives have the formula

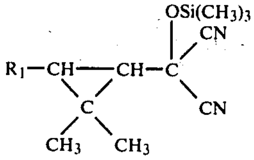

or, (I)

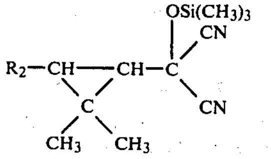

(II)

wherein $R_1$ is

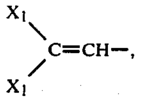

$R_2$ is

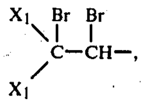

and $X_1$ is halogen.

The term "halogen" denotes fluorine, chlorine, bromine or iodine, with chlorine or bromine being preferred.

The compounds of the formulae I and II are obtained by methods which are known per se, e.g. as follows:

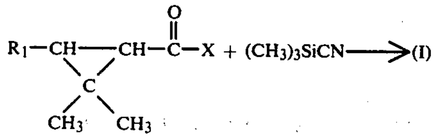

(1)

(III) (IV)

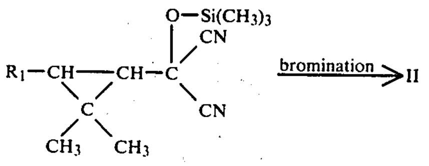

(2)

(I)

In formula III, $R_1$ has the same meaning as in formula I and X is chlorine or bromine.

Processes 1 and 2 are carried out at a reaction temperature in the range from 0° to 110° C., with the preferred temperature range being from 10° to 80° C., under normal or elevated pressure, and preferably in an inert solvent or diluent. Examples of suitable solvents or diluents are: ethers such as diethyl ether, dipropyl ether, dioxane, dimethoxyethane and tetrahydrofurane; aliphatic, aromatic and halogenated hydrocarbons, especially benzene, toluene, xylene, chloroform and chlorobenzene.

The starting materials of the formulae III and IV are known or they can be obtained by methods analogous to known ones.

The compounds of the formulae I and II exist in the form of different optically active isomers if inhomogeneous optically active starting materials are used in the reaction. The different mixtures of isomers can be separated into the individual isomers by known methods. The compounds of the formulae I and II are to be understood as comprising both the individual isomers and the mixtures thereof.

The compounds of the formulae I and II are intermediates for the production of insecticidal and acaricidal cyclopropanecarboxylates of the formula

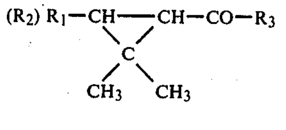

(V)

wherein $R_1$ and $R_2$ are as defined for formulae I and II and $R_3$ is an alcohol radial known in pyrethroid chemistry.

The properties of compounds of the formula V are described in the literature (cf. for example Nature 246, 169-170 (1973); Nature 248, 710-711 (1974); Proceedings 7th British Insecticide and Fungicide Conference, 373-78(1975); J. Agr. Food Chem. 23, 115 (1973); U.S. Pat. No. 3,961,070; German Offenlegungsschriften Nos. 2 553 991, 2 439 177, 2 326 077, 2 641 648).

EXAMPLE 1

Production of 1-(dicyano-trimethylsiloxy)methyl-2,2-dimethyl-3-(2,2-dichlorovinyl)cyclopropane 15 g of 3-(2,2-dichlorovinyl)-2,2-dimethylcyclopropanecarboxylic acid chloride are added dropwise to 15 ml of trimethylsilyl cyanide under dry inert gas. The solution obtained is stirred for 16 hours at 20° C. Distillation affords the compound of the formula

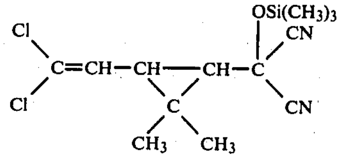

with a refractive index of $n_D^{20}=1.4765$ and a boiling point of 75°-80° C./0.1 torr. The following compound is obtained in similar manner:

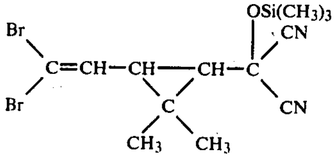

NMR 6.1 and 6.4 ppm (d, 1H); 1-2 ppm (m, 6H); 0.3 ppm (S, 9H).

EXAMPLE 2

Production of 1-(dicyano-trimethylsiloxy)methyl-2,2-dimethyl-3-(1,2-dibromo-2,2-dichloroethyl)cyclopropane 4.7 g of 1-(dicyano-trimethylsiloxy)methyl-2,2-dimethyl-3-(2,2-dichlorovinyl)cyclopropane (according to Example 1) are heated in 30 ml of carbon tetrachloride to 70° C. under nitrogen. After addition of a trace of azo-bis-isobutyronitrile, the reaction mixture is stirred for two hours at 70° C. Bulb tube distillation (oven temperature 120° C./0.1 torr) affords the compound of the formula

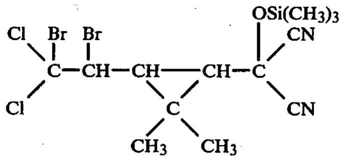

with a refractive index of $n_D^{20}=1.5200$. The following compound is also obtained in similar manner:

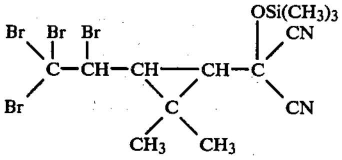

$n_D^{20°} = 1.5341$.

EXAMPLE 3

Production of α-cyano-3-phenoxybenzyl-2,2-dimethyl-3-(2,2-dichlorovinyl)cyclopropane-1-carboxylate To a solution of 1 g of 1-(dicyano-trimethylsiloxy)-methyl-2,2-dimethyl-3-(2,2-dichlorovinyl)cyclopropane and 0.64 g of 3-phenoxybenzaldehyde in 3 ml of tetrahydrofurane are added 10 mg of tetrabutylammonium fluoride . 3 $H_2O$. The reaction mixture is left to stand for 18 hours at 20° C. and then diluted with ether. The organic phase is washed with 10% potassium carbonate solution, potassium bicarbonate solution and with brine, and dried over magnesium sulfate. The solvent is removed and the residue is chromatographed with hexane/tetrahydrofurane (95:5) as eluant, affording the compound of the formula

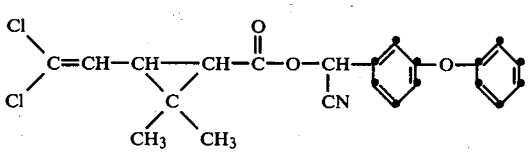

with a refractive index of $n_D^{20°}=1.5680$.

The compounds of the formulae

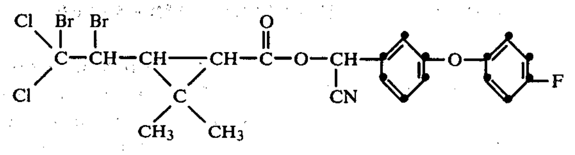

$n_D^{20°} = 1.5753$

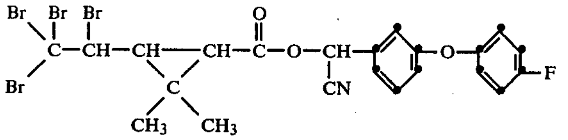

$n_D^{30°} = 1.5840$ are obtained in similar manner from the compound of Example 2 and 3-(p-fluorophenoxy)benzaldehyde.

What is claimed is:

1. A 1-(dicyano-trimethylsiloxy)methyl-2,2-dimethylcyclopropane derivative of the formula

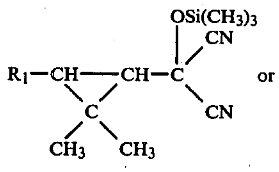 or 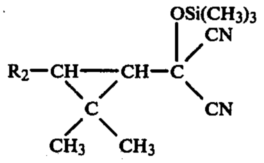

wherein $R_1$ is

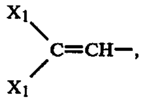, $R_2$ is 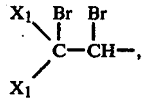, and $X_1$ is halogen.

2. The compound according to claim 1 of the formula

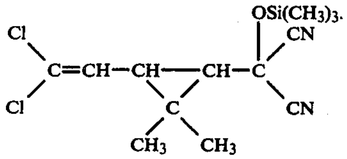.

3. The compound according to claim 1 of the formula

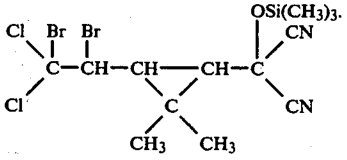.

4. A process for the production of compounds according to claim 1, which process comprises (a) reacting a compound of the formula

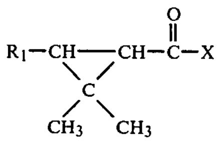
wherein $R_1$ is as defined for claim 1 and X is chlorine or bromine, with the compound of the formula
$(CH_3)_3SiCN$
or
(b) brominating a compound of the formula
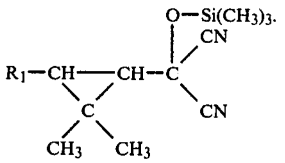
5. The compound according to claim 1 of the formula
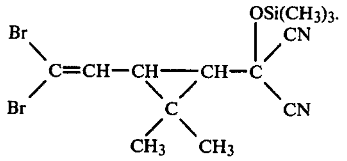
6. The compound according to claim 1 of the formula
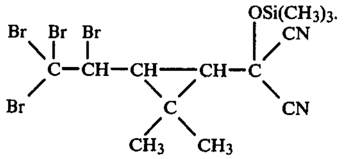
* * * * *